United States Patent
Itoh et al.

(10) Patent No.: US 10,758,583 B2
(45) Date of Patent: Sep. 1, 2020

(54) PROCESSED FOOD AND PHARMACEUTICAL COMPOSITION HAVING WATERMELON SPROUT-DERIVED SUBSTANCES AS MAIN INGREDIENTS

(71) Applicants: KINKI UNIVERSITY, Osaka (JP); HAGIHARA FARM PRODUCTION INSTITUTE CO., LTD., Nara (JP)

(72) Inventors: Tomohiro Itoh, Mie (JP); Toshiharu Hashizume, Nara (JP)

(73) Assignees: KINKI UNIVERSITY, Osaka (JP); HAGIHARA FARM PRODUCTION INSTITUTE CO., LTD., Nara (JP)

( * ) Notice: Subject to any disclaimer, the term of this patent is extended or adjusted under 35 U.S.C. 154(b) by 0 days.

(21) Appl. No.: 16/073,450

(22) PCT Filed: Jan. 27, 2017

(86) PCT No.: PCT/JP2017/002982
§ 371 (c)(1),
(2) Date: Jul. 27, 2018

(87) PCT Pub. No.: WO2017/131175
PCT Pub. Date: Aug. 3, 2017

(65) Prior Publication Data
US 2019/0343909 A1 Nov. 14, 2019

(30) Foreign Application Priority Data
Jan. 29, 2016 (JP) .................. 2016-015721

(51) Int. Cl.
*A61K 36/42* (2006.01)
*A23L 33/105* (2016.01)
*A61P 35/00* (2006.01)

(52) U.S. Cl.
CPC ............ *A61K 36/42* (2013.01); *A23L 33/105* (2016.08); *A61P 35/00* (2018.01); *A23V 2002/00* (2013.01); *A61K 2236/15* (2013.01); *A61K 2236/333* (2013.01); *A61K 2236/35* (2013.01)

(58) Field of Classification Search
CPC . A23L 33/105; A61K 2800/522; A61K 36/42; A61K 8/97; A61K 2236/15; A61K 2236/333; A61K 2236/35; A61Q 19/00; A61Q 19/007; A61Q 19/10; A61Q 5/02; A61Q 5/12; A61Q 7/00; A61P 35/00; A23V 2002/00
See application file for complete search history.

(56) References Cited

U.S. PATENT DOCUMENTS

2007/0218150 A1 9/2007 Akashi et al.

FOREIGN PATENT DOCUMENTS

| JP | 2003-61615 A | 3/2003 |
|---|---|---|
| JP | 2005-206495 A | 8/2005 |
| JP | 2010-64984 A | 3/2010 |
| JP | 2014-224085 A | 12/2014 |
| WO | 2005/105126 A1 | 11/2005 |

OTHER PUBLICATIONS

Hoyoku Nishino et al., "Carotenoids in cancer chemoprevention", Cancer and Metastasis Reviews, vol. 21, 2002, pp. 257-264.
Karin Muller et al., "Carotenoids Induce Apoptosis in the T-lymphoblast Cell Line Jurkat E6.1", Free Radical Research, vol. 36, No. 7, ISSN 1071-5762, 2002, pp. 791-802.
Masaki Kyokon et al., "Phytol Kanren Kagobutsu no Kozo to ko Shuyo Kassei no Sokan ni Tsuite", Journal of the Agricultural Chemical Society of Japan, vol. 74, special extra issue, Nen Taikai (Tokyo) Koen Yoshishu ISSN 0002-1407, along with an English language machine translation , Mar. 5, 2000, pp. 67.
Yukihiro Yamamoto et al., "Preparation of Phosphatidylated Terpenes via Phospholipase D-Mediated Transphophatidylation", Journal of the American Oil Chemists' Society, vol. 85, No. 4, Apr. 2008, pp. 313-320.
R. Chakravarthy et al., "In vitro floral bud synthesis and multiple shoot regeneration studies in watermelon (Citrullus lanatus) from seed explants", Research & Reviews in BioSciences, vol. 7, No. 2, ISSN 0974-7532 , 2013, pp. 44-46.
J.L. Jeffery and S.R. King, "A New Approach to Nutritive Analysis Using Watermelon as a Case Study", Acta Horticulturae, No. 841, ISSN 0567-7572, Aug. 2009, pp. 533-536.
Tomohiro Itoh et al., "Suika Sprout ni yoru Hito Hakketsubyo Saibo Kabu Jurkat Saibo no Zoshoku Yokusei Kiko ni Tsuite", Proceedings of the Annual Meeting of Japan Society for Bioscience Biotechnology, and Agrochemistry, vol. 2016, ISSN 2186-7976, along with an English language machine translation, Mar. 5, 2016, pp. 2E104.
International search Report issued with respect to Patent Application No. PCT/JP2017/002982, dated Apr. 4, 2017.
International Preliminary Report on Patentability issued with respect to Patent Application No. PCT/JP2017/002982, dated Jul. 31, 2018.

*Primary Examiner* — Aaron J Kosar
(74) *Attorney, Agent, or Firm* — Greenblum & Bernstein, P.L.C.

(57) ABSTRACT

A so-called molecular-targeted drug acting on a signal transduction pathway in a cell has been developed. However, a side effect of the molecular-targeted drug is not negligible for a patient. Thus, there has been a demand for a substance that exhibits a significant growth inhibitory effect on a cancer cell with fewer side effects as a health food and a pharmaceutical composition. It has been found that a hexane extract fraction of a watermelon sprout has an effect of specifically inhibiting the cell growth of the cancer cell and such an effect is primarily caused by phytol and lutein. A processed food and pharmaceutical composition having these substances as main components can exert an anticancer action without causing side effects.

8 Claims, 9 Drawing Sheets

PROCESSED FOOD AND PHARMACEUTICAL COMPOSITION HAVING WATERMELON SPROUT-DERIVED SUBSTANCES AS MAIN INGREDIENTS

FIELD

The present invention relates to a processed food and pharmaceutical composition including a watermelon sprout-derived substance.

BACKGROUND

Recently, functional studies of various sprouts, such as a soybean sprout, a daikon radish sprout, an alfalfa sprout, a broccoli sprout, a pea sprout, and a red water pepper, have been actively carried out. For example, it is reported that a production of vitamin C after germination significantly contributes to an antioxidant activity in a sprout.

Further, Patent Literature 1 discloses: a health food for preventing cancer, which contains, as an active component, a daikon radish seed or sprout, an aqueous, organic solvent, or organic solvent/aqueous based extract thereof, or a compound contained in the extract or a derivative thereof; a health drink for preventing cancer, which contains, as an active component, a raw daikon radish sprout juice, a daikon radish sprout juice from concentrate, or an aqueous, organic solvent, or organic solvent/aqueous based extract of a daikon radish sprout or seed; and a medicinal composition for preventing cancer, which contains, as an active component, a daikon radish seed or sprout, an aqueous, organic solvent, or organic solvent/aqueous based extract thereof, or a compound contained in the extract or a derivative thereof.

Further, Patent Literature 2 discloses that arctigenin contained in a burdock sprout inhibits the generation of a cancer stem cell.

CITATION LIST

Patent Literature

Patent Literature 1: Japanese Patent Application Laid-Open No. 2005-206495
Patent Literature 2: Japanese Patent Application Laid-Open No. 2014-224085

SUMMARY

Technical Problem

As is evident from Patent Literatures, recent studies show that a sprout has an anticancer activity as well as a previously known antioxidant activity. A cancer treatment includes chemotherapy in addition to surgery. Currently, a so-called molecular-targeted drug acting on a signal transduction pathway in a cell has been developed. However, a side effect of the molecular-targeted drug is not negligible for a patient. Thus, there has been a demand for a substance that exhibits a significant growth inhibitory effect on a cancer cell with fewer side effects as a health food and a pharmaceutical composition.

An action mechanism of a substance extracted from a natural product such as a sprout is not known in many cases. However, such a substance can be expected to have fewer side effects judging from accumulated experience as a food.

However, it is not reported whether the sprout derived substances in Patent Literatures have a specific inhibitory action on a cancer cell.

Solution to Problem

In a course of investigation on an effect of a sprout-derived substance, the inventors of the present invention have found that a watermelon sprout-derived substance can specifically inhibit the growth of a cancer cell, thereby completing the invention including a health food and a pharmaceutical composition.

More specifically, a pharmaceutical composition according to the present invention is a cancer cell growth inhibitor including at least one of phytol and lutein as a main component.

Further, a processed food according to the present invention includes at least one of phytol and lutein as a main component.

Advantageous Effects of Invention

An extract of the watermelon sprout using a nonpolar solvent specifically inhibits the growth of a cancer cell (in particular, a human leukemic cell) without substantially affecting a healthy cell. Further, it has been found that phytol and lutein make a particularly large contribution in the nonpolar solvent extract fraction of the watermelon sprout. Thus, the processed food and pharmaceutical composition (a cancer cell growth inhibitor) including at least one of phytol and lutein as a main component are effective as a prophylactic or therapeutic drug of cancer.

DESCRIPTION OF EMBODIMENTS

Figure 1:
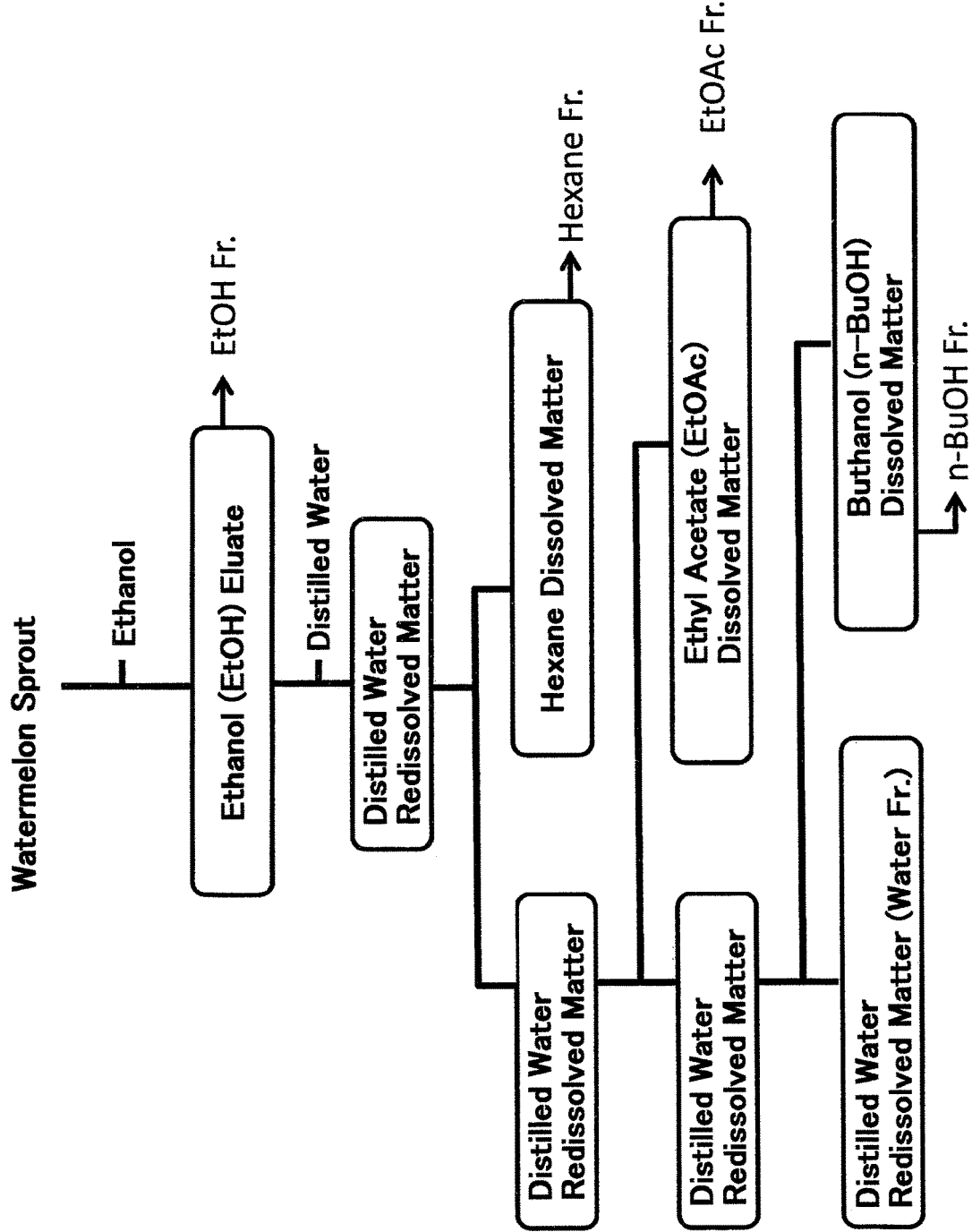
FIG. 1 is a diagram showing a procedure of making an extract of a watermelon sprout.

Hereinafter, the present invention will be described by way of Examples. Note that the following description exemplifies an embodiment and an Example of the present invention and the present invention is not limited to the following description. The following description may be changed or modified within a scope not departing from the gist of the present invention.

A processed food and pharmaceutical composition according to the present invention include at least one of phytol and lutein as a main component. Further, a nonpolar solvent extract fraction of a watermelon sprout may be used as a main component. This is because, as shown in Examples described below, the nonpolar solvent extract fraction of the watermelon sprout has an effect of specifically inhibiting the growth of a cancer cell and phytol and lutein in the nonpolar solvent extract fraction significantly contribute to such an effect.

Note that, in the present specification, the nonpolar solvent extract fraction of the watermelon sprout, phytol, lutein, and derivatives of phytol and lutein are collectively referred to as an "effective component of the present invention." Further, an "effect of specifically inhibiting the growth of a cancer cell" exhibited by the effective component of the present invention is referred to as an "effect of the effective component of the present invention."

In the present specification, the processed food and pharmaceutical composition only needs to include the "main component" in an amount required for exerting the effect of the effective component of the present invention. That is, the processed food and pharmaceutical composition may include a component having an effect other than the effect of the effective component of the present invention.

<Nonpolar Solvent Extract Fraction of Watermelon Sprout>

In the present invention, the watermelon refers to an annual climbing plant of the family Cucurbitaceae under a scientific name of *Citrullus lanatus*. The watermelon may be from the wild or obtained by breeding. In particular, a breed, such as "Matsuribayashi 777" and "Harunodanran" in Japanese, is preferably used.

The watermelon sprout refers to a sprout obtained by germinating a watermelon seed. In particular, the watermelon sprout is preferably 10- to 20-day-old after sowing. The watermelon seed is not exposed to the sunlight before germination, but the sprout is exposed to the sunlight after germination for growth. The watermelon seed is applied with only water for germination, but the sprout is applied with a liquid fertilizer containing a nutrient, such as nitrogen, phosphoric acid, and potassium, after germination. A suitable germination temperature is 25° C. to 30° C. Note that the sprout in use may be freeze-dried after harvest.

All parts of the harvested sprout, a root, a stem, and a leaf, may be used. In particular, the leaf part contains a significant amount of phytol and lutein considered to be the effective component of the processed food or pharmaceutical composition according to the present invention.

In an extraction method, a material obtained by ethanol extraction and water extraction is subjected to nonpolar solvent extraction. Examples of the nonpolar solvent that can be preferably used may include ketones such as acetone and methyl ethyl ketone, ethers such as diethyl ether, and aliphatic hydrocarbons such as hexane and pentane. Of these, hexane is preferably used.

The extraction method for obtention may include a pre-treatment step of washing and crushing a material, a step of obtaining an extract liquid by immersing the crushed material in the nonpolar extraction solvent, and a step of filtering the extract liquid. The extraction method may further include a step of drying a filtrate.

As shown in Examples described below, it has been found that phytol and lutein included in the nonpolar solvent extract fraction of the watermelon sprout are the substance that exerts the growth inhibitory effect on a cancer cell. These substances as well as their derivatives exert the effect of the effective component of the present invention.

For example, phytanic acid ($C_{20}H_{40}O_2$; CAS Number: 14721-66-5) is qualified as a phytol derivative. Further, a compound in which a hydroxyl group of phytol or lutein is methylated or methoxylated is expected to exert the effect of the effective component of the present invention.

Thus, the method of extracting the effective component of the present invention from the watermelon sprout may include a step of obtaining the derivative from the whole filtered or dried extract.

<Phytol and Lutein>

Phytol ($C_{20}H_{40}O$; CAS Number: 7541-49-3) and lutein ($C_{40}H_{56}O_2$; CAS Number: 127-40-2) are represented by the formula (1) and the formula (2), respectively.

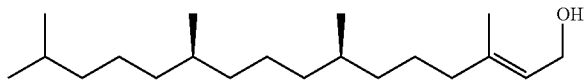

[Chemical Formula 1]

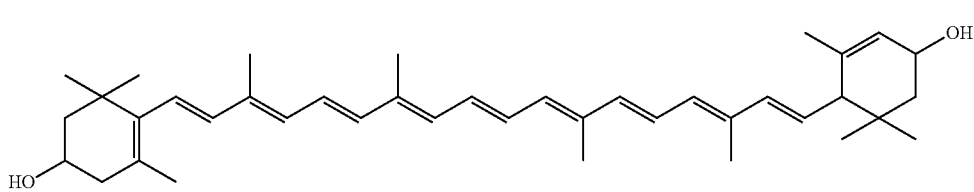

[Chemical Formula 2]

As shown in Examples described below, a substance that has an effect of specifically inhibiting the growth of a cancer cell is these two substances in the nonpolar solvent extract fraction of the watermelon sprout. In particular, phytol significantly exerts such an effect. Further, the derivatives of these substances are expected to exert the similar effect and thus included in the effective component of the present invention.

<Processed Food>

The processed food according to the present invention includes the effective component of the present invention as a main component. Examples of a form of the processed food not only include a general processed food, such as a candy, a biscuit, a cookie, a rice cracker, a bread, a noodle, fish- and meat-paste products, a tea, a refreshing beverage, a milk beverage, a whey beverage, a lactic acid bacteria beverage, a yogurt, and an ice cream, but also include an extract, such as a viscous extract, a dry extract, a capsule, a granule, a powder, a tablet, a liquid, an infusion, a decoction, a troche, a fluid extract, and a tincture, and an alcoholic beverage.

<Pharmaceutical Composition>

The pharmaceutical composition according to the present invention includes the effective component of the present invention as a main component. Examples of a form of the drug include a capsule, a granule, a solution, an emulsion, a suspension, a powder, a tablet, a liquid, an infusion, a decoction, a troche, a fluid extract, a tincture, an eye drop, a nasal drop, an ointment, a cream, a lotion, an injection, and a suppository.

These formulations are formed into a preparation in accordance with a conventional method using, as a main component, a known auxiliary agent that may be ordinarily used in the art of pharmaceutical preparation, such as an excipient, a binder, a disintegrant, a lubricant, a stabilizer, a flavoring agent, a solubilizer, a suspending agent, a coating agent, and a diluent. Further, the pharmaceutical composition of the present invention may include other pharmacological active components in addition to the effective component of the present invention.

Examples of a solid formulation include a powder, a granule, a tablet, a capsule, and a sugar-coated tablet. The solid formulation including the effective component of the present invention as an active component may also include a diluent (for example, lactose, dextrose, sucrose, cellulose, a corn starch, a potato starch, etc.), a lubricant (for example, silica, talc, stearic acid, magnesium stearate, calcium stearate, polyethylene glycol, etc.), a binder (for example, starches, gum arabic, gelatin, methyl cellulose, carboxymethyl cellulose, polyvinylpyrrolidone, etc.), a dispersant (for example, a starch, alginic acid, an alginic acid salt, etc.), a saturant, a colorant, a sweetener, a wetting agent (for example, lecithin, polysorbate, a lauryl sulfuric acid salt, etc.), and the like. These components may be formed into a preparation by a known method, such as, for example, mixing, granulation, tableting, and sugar-coating.

A liquid formulation may be formed into, for example, a syrup, a solution, an emulsion, and a suspension. As a carrier, the suspension and the emulsion may include, for example, natural rubber, agar, sodium alginate, pectin, methylcellulose, carboxymethyl cellulose, a polyvinyl alcohol, and the like.

EXAMPLES

1. Preparation of Test Sample

Sprouts of a watermelon of CS species in an amount of 3 kg (wet weight) were crushed and 5 L of ethanol was added to the crushed matter. A mixture was stirred at a normal temperature to prepare an ethanol eluate. This operation was repeated three times. The liquid eluate was concentrated and dried under a reduced pressure using a rotary evaporator.

After evaluating a Jurkat cell growth inhibitory activity, the ethanol eluate (EtOH Fr.) was redissolved with distilled water. Then, the dissolved matter was subjected to a solvent fractionation method using hexane (Hexane Fr.), ethyl acetate (EtOAc Fr.), and butanol (n-BuOH Fr.) in this order to prepare respective elution fractions and a distilled water dissolved matter (Water Fr.). FIG. 1 shows a procedure of the extraction.

2. Cell Culture

A human T-cell leukemia cell line Jurkat cell was obtained from the Independent Administrative Institution RIKEN BioResource Center (Tsukuba-shi, Ibaraki-ken). The cell was cultured in a RPMI 1640 medium (Wako Pure Chemical Industries, Ltd., Osaka-shi, Osaka-fu) containing 10% fetal bovine serum (Thermo Fisher Scientifics, K.K., MA, USA), 100 U/mL penicillin, and 100 μg/mL streptomycin (both from Life Technologies, Carlsbad, Calif., USA) at 37° C. in an environment of 95% air and 5% $CO_2$.

3. Effects of Respective Fractions and Isolated Substances Extracted from Watermelon Sprout Ethanol Solution on Growth of Human T-Cell Leukemia Cell Line Jurkat Cell The Jurkat cells were adjusted to $1 \times 10^5$ cells/mL and seeded in a 24-well multi-well plate (Thermo Fisher Scientifics, K.K.) by 500 μL per well. After seeding, the cells in each well were treated with the watermelon sprout ethanol eluate (EtOH Fr.) at final concentrations of 10, 25, 50, 100, 200, and 300 μg/ml, or one of the hexane (Hexane Fr.), ethyl acetate (EtOAc Fr.), and butanol (n-BuOH Fr.) eluates, and the distilled water dissolved matter (Water Fr.) at final concentrations of 25, 50, and 100 μg/ml, and cultured. At 24, 48, and 72 hours after the sample treatment, the cells were stained with trypan blue (Life Technologies) to count live cells using a hemacytometer.

4. Cell Cycle Analysis

The Jurkat cells (adjusted to $1 \times 10^5$ cells/mL) were seeded in a 6-well plate by 3 mL per well to perform a preculture for 2 hours. After performing the 2-hour preculture, the Hexane Fr. was added to the cells at a final concentration of 10 μg/ml and the cells were cultured. At 12, 24, 48 and 72 hours after cultivation, the cells were collected, washed twice with PBS, and then added with 70% ethanol to fix the cells at −20° C. for overnight.

Next day, the fixed cells were centrifuged at 300×g and a cell pellet was washed twice with PBS. After washing, a cell staining reagent included in a Muse (registered trademark) Cell Cycle Kit (Millipore, Darmstadt, Germany) in an amount of 200 μL was added to stain the cells under a light-shielded environment at a room temperature for 30 minutes. Then, a cell cycle analysis was performed using Muse (registered trademark) Cell Analyzer (Millipore).

5. Effect of Hexane Fr. Extracted from Watermelon Sprout Ethanol Solution on Human Normal Lymphoid Cell Human peripheral blood was subjected to a Ficoll density gradient separation method (Ficoll-paque PLUS, GE healthcare UK Ltd., England) to prepare a human normal lymphoid cell. The human normal lymphoid cells were adjusted to $1 \times 10^5$ cells/mL and seeded in a 96-well multi-well plate (Thermo Fisher Scientifics, K.K.) by 100 μL per well. After seeding, the cells in each well were treated with the watermelon sprout hexane eluate at a final concentration of 10 μg/mL, and cultured. At 48 hours after the sample treatment, the cells were stained with trypan blue (Life Technologies) to count live cells using the hemacytometer.

6. Isolation of Effective Component

Figure 2:
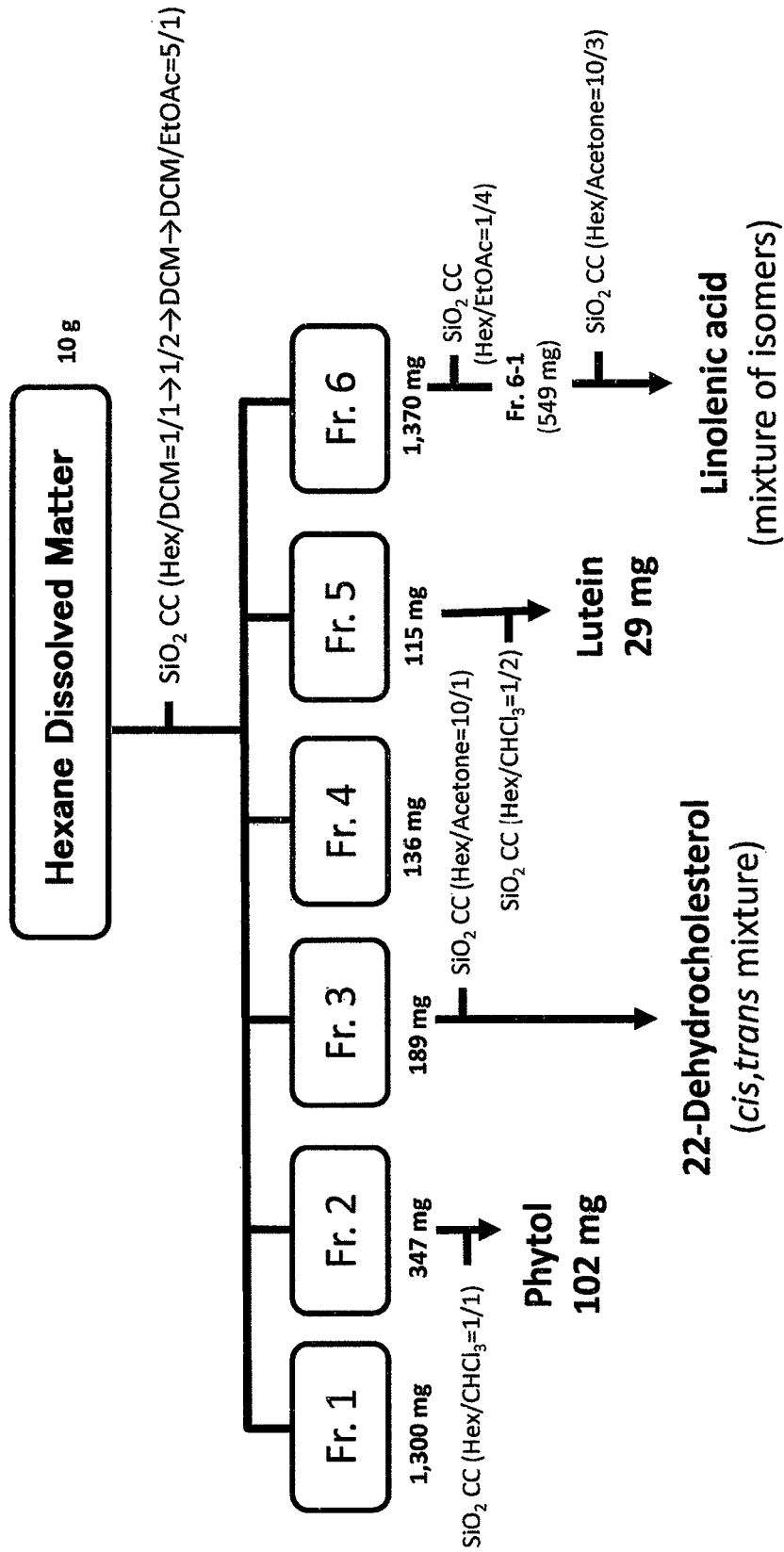
FIG. 2 is a diagram showing an extraction procedure for further isolating hexane fractions.

The effective component in the hexane eluate was isolated. FIG. 2 shows its procedure. The hexane eluate (Hexane Fr.) shown in FIG. 1 in an amount of 10 g was subjected to a silica gel chromatography and eluted with hexane (Hex):dichloromethane (DCM)=1:1, 1:2, dichloromethane, and dichloromethane:ethyl acetate=5:1 to obtain 6 fractions (Fr. 1 to Fr. 6). In FIG. 2, this operation was represented by $SiO_2CC$ (Hex/DCM=1/1→1/2→DCM-→DCM/EtOAc=5/1). "$SiO_2CC$" refers to the silica gel chromatography.

The six fractions were examined for the effect on the Jurkat cells and four fractions (Fr. 2, Fr. 3, Fr. 5, and Fr. 6) exerting the effect were selected. These four fractions were further subjected to various kinds of silica gel chromatography to isolate 4 compounds (phytol, lutein, 22-dehydrocholesterol, and linolenic acid).

More specifically, the second fraction Fr. 2 was further separated with hexane (Hex):chloroform (CHCl$_3$)=1:1 to obtain phytol. Further, the third fraction was separated with hexane (Hex):acetone=10:1 to obtain 22-dehydrocholesterol.

Further, the fifth fraction was separated with hexane (Hex):chloroform (CHCl$_3$)=1:2 to obtain lutein. Further, the six fraction was first separated with hexane (Hex):butyl acetate (EtOAc)=1:4, and then with a solution of hexane (Hex):acetone=10:3 to obtain linolenic acid.

7. Effect of Hexane Fr. Extracted from Watermelon Sprout Ethanol Solution on Growth of Various Human Cancer Cells Human cervical cancer-derived cell line HeLa cells, human alveolar basal epithelial adenocarcinoma A549 cells, human gastric cancer-derived cell line KatoIII cells, and human hepatoma-derived cell line HepG2 cells were each adjusted to 1×10$^5$ cells/mL and seeded in a 96-well multi-well plate (Thermo Fisher Scientifics, K.K.) by 100 µL per well. After seeding, the hexane eluate (Hexane Fr.) was added to the cells at final concentrations of 2.5, 5, 10, 25, 50, 100, and 200 µg/mL, and the cells were cultured.

At 24, 48, and 72 hours after the sample treatment, the cell culture medium was removed and replaced with a fresh medium containing 10% WST-1 reagent (Takara bio, Kusatsu, Shiga) and the cells were cultured for 45 minutes. After 45 minutes, the medium in an amount of 50 µL was transferred to a fresh 96-well multi-well plate. After adding 50 µL of distilled water to the medium, an absorbance of the mixture at 440 nm ($A_{440}$) was measured. A ratio (%) of living cells was obtained by the following formula.

Ratio of living cells (%)={($A_{440}$ of hexane-treated cancer cells)/($A_{440}$ of untreated cancer cells)}× 100

<Experimental Results>

[Effect of Watermelon Sprout Ethanol Eluate on Growth of Human T-Cell Leukemia Cell Line Jurkat Cell]

Figure 3:
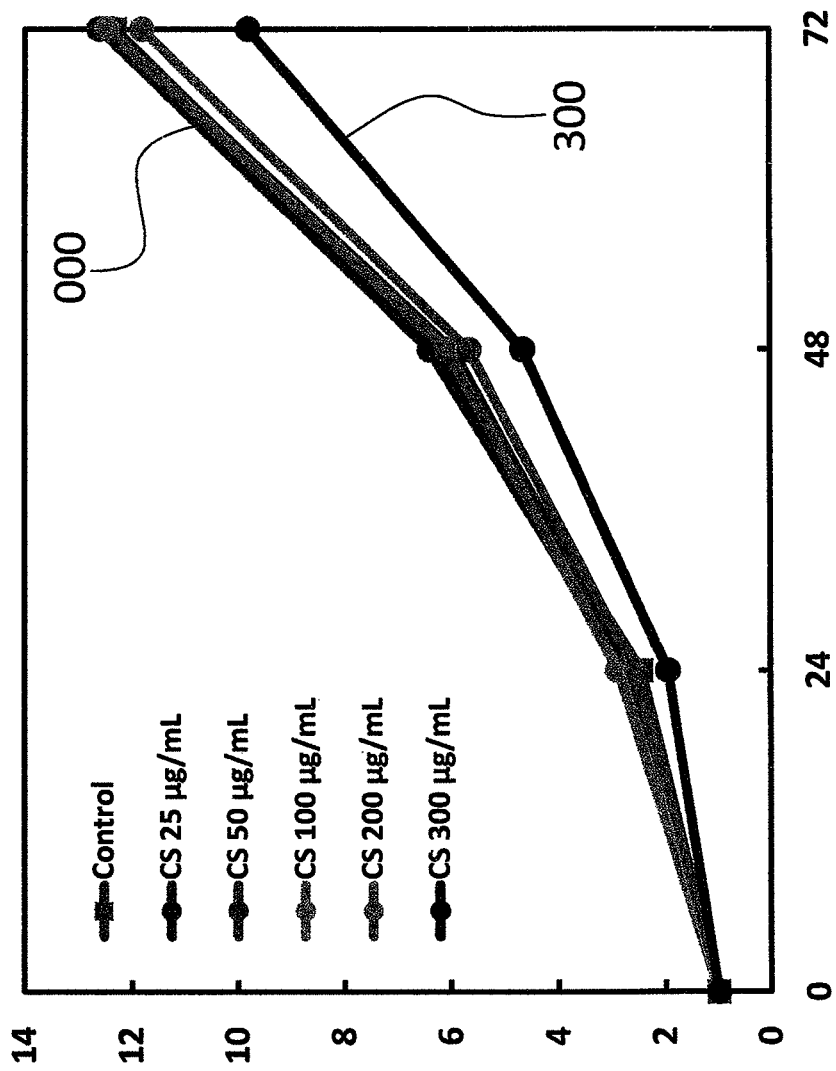
FIG. 3 is a graph showing an effect of an ethanol eluate of the watermelon sprout on the growth of a human T-cell leukemia cell line Jurkat cell.

The Jurkat cells were treated with the watermelon sprout ethanol eluate (EtOH Fr.) at final concentrations of 10, 25, 50, 100, 200, and 300 µ/mL. The results thereof are shown in FIG. 3. A lateral axis indicates a treatment time (hours) and a vertical axis indicates the number of surviving cells (10$^5$×cells/mL). It was confirmed that, at 48 hours or later after treatment, the growth was significantly inhibited in a cell group treated with 300 µg/mL (symbol 300) as compared to an untreated group (symbol 000).

[Effect of Subfractions of Watermelon Sprout Ethanol Eluate Obtained by Using Various Solvents on Growth of Human T-Cell Leukemia Cell Line Jurkat Cell]

Figure 4:
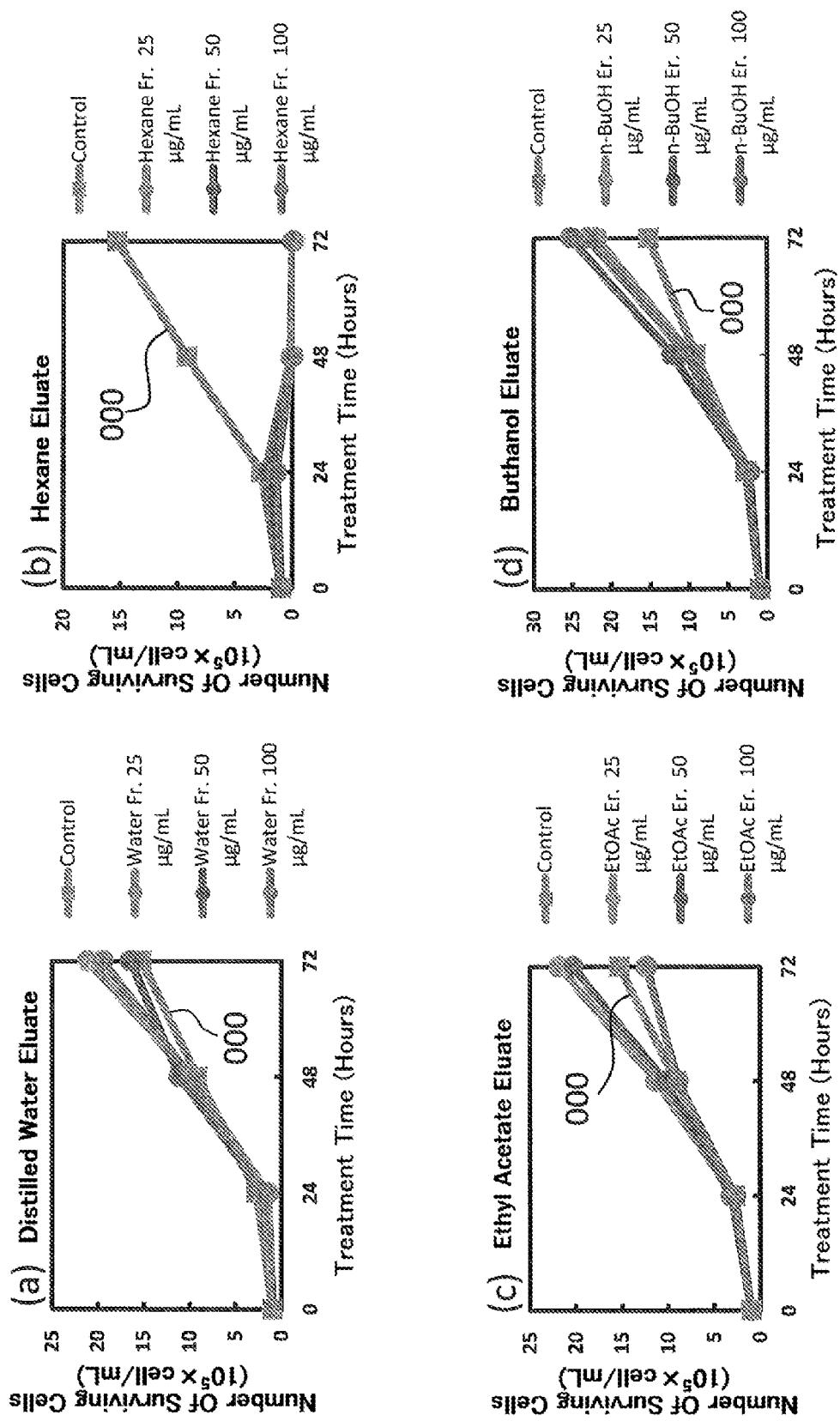
FIG. 4 is graphs showing effects of subfractions of the ethanol eluate of the watermelon sprout obtained by using various solvents on the growth of the human T-cell leukemia cell line Jurkat cell.

The concentrated and dried ethanol eluate was redissolved with distilled water. Then, the resulting matter was subjected to a solvent fractionation method using hexane (Hexane Fr.) (FIG. 4(b)), ethyl acetate (EtOAc Fr.) (FIG. 4(c)), and butanol (n-BuOH Fr.) (FIG. 4(d)) to prepare respective dissolved matters and a distilled water redissolved matter (Water Fr.) (FIG. 4(a)). Note that these dissolved matters may be referred to as extract fractions.

In each graph, a lateral axis indicates a treatment time (hours) and a vertical axis indicates the number of surviving cells (10$^5$×cells/mL). The Jurkat cells were treated with these extract fractions at final concentrations of 25, 50, and 100 µg/mL and the cell number was counted at 24, 48, and 72 hours after treatment. The result confirmed that the hexane elution fraction (Hexane Fr.) (FIG. 4(b)) exhibited a significant growth inhibitory activity. Specifically, adding the hexane elution fraction in an amount of 24 µg/mL or more prevented an increase in the cell number as compared to a control (symbol 000). Other fractions (FIGS. 4(a), (c), and (d)) hardly inhibited the growth of the Jurkat cells.

[Effect of Hexane Dissolved Matter on Growth of Human T-Cell Leukemia Cell Line Jurkat Cell]

Figure 5:
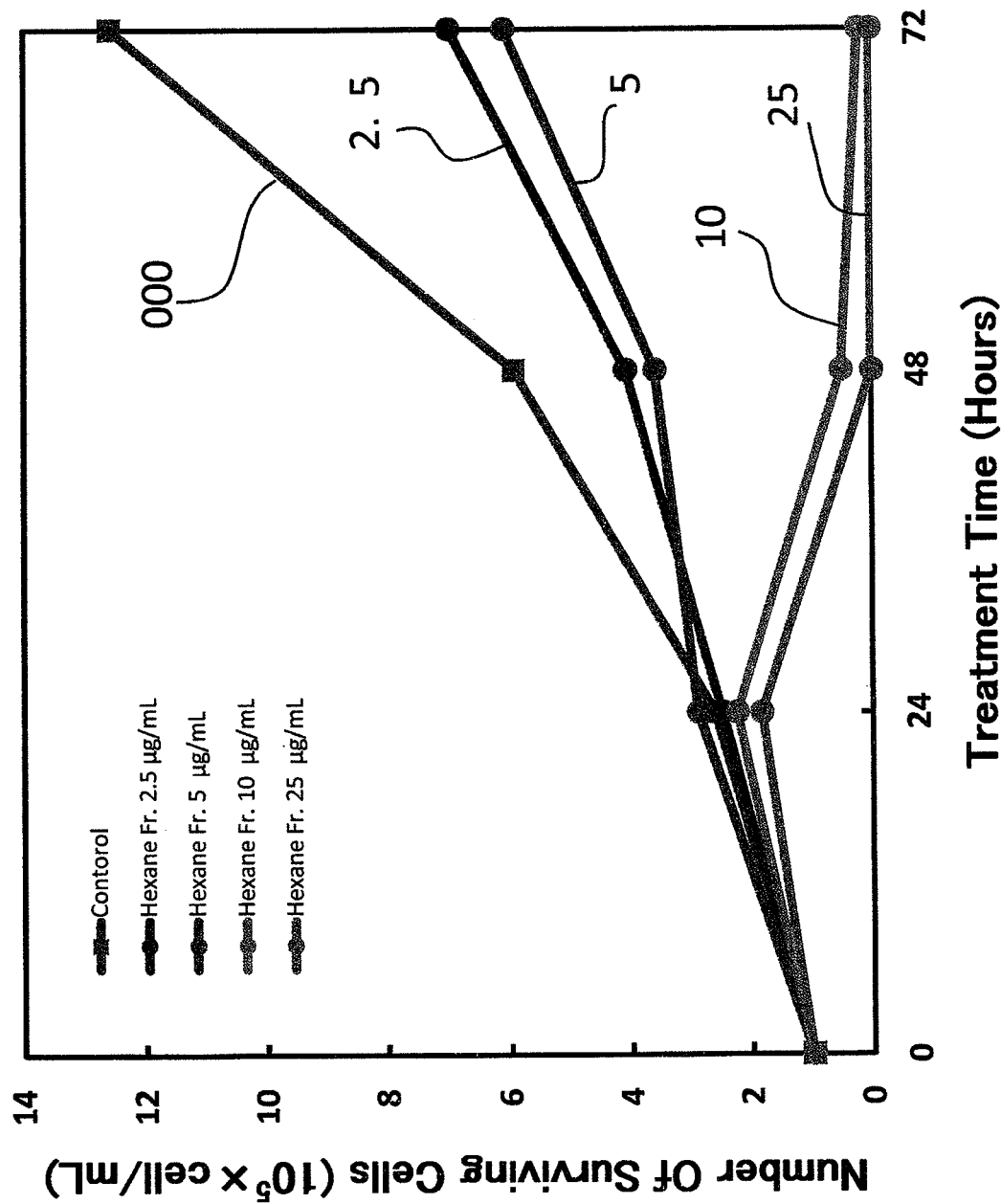
FIG. 5 is a graph showing an effect of a hexane eluate on the growth of the human T-cell leukemia cell line Jurkat cell.

Since the hexane extract fraction exhibited a significant growth inhibitory effect on the Jurkat cells, the growth inhibitory effect on the Jurkat cells was examined by lowering the concentration of the hexane extract fraction. The result thereof is shown in FIG. 5. In FIG. 5, a lateral axis indicates a treatment time (hours) and a vertical axis indicates the number of surviving cells (10$^5$×cells/mL).

Lines in the graph show data of the hexane dissolved matter at a concentration of 2.5 µg/mL (symbol 2.5), 5 µg/mL (symbol 5), 10 µg/mL (symbol 10), and 25 µg/mL (symbol 25), and data of a control (symbol 000).

Referring to FIG. 5, the hexane extract fraction inhibited the growth of the Jurkat cells in a treatment concentration-dependent manner. Most of the Jurkat cells died out at 48 hours after a 10 µg/mL treatment (symbol 10) as was the case with a 25 µg/mL treatment (symbol 25).

[Effect of Watermelon Sprout-Hexane Dissolved Matter Treatment on Cell Cycle of Jurkat Cell]

Figure 6:
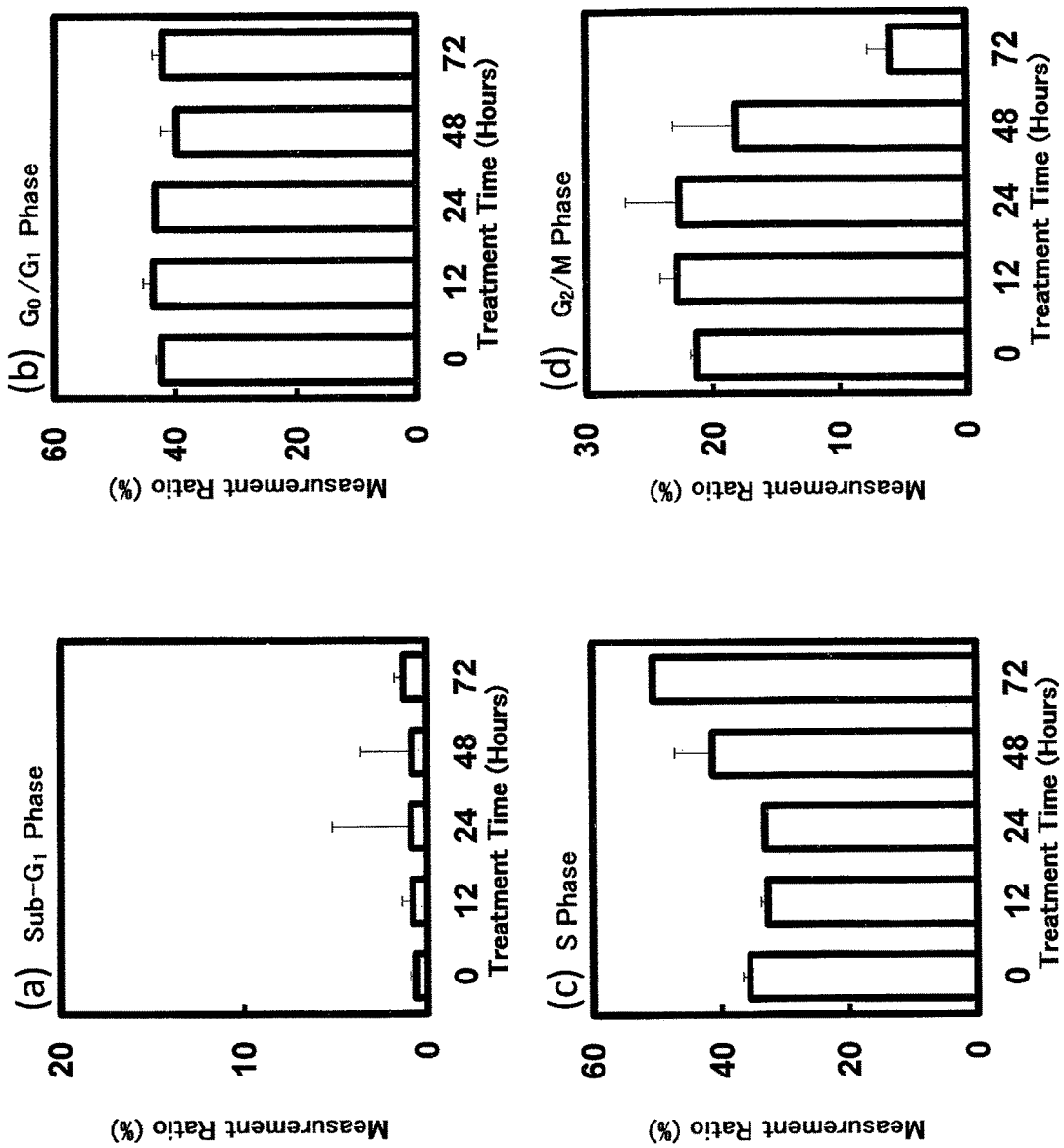
FIG. 6 is graphs showing an effect of a watermelon sprout-hexane eluate treatment on a cell cycle of the Jurkat cell.

An effect of the hexane extract fraction treatment on a cell cycle of the Jurkat cell was examined. The result thereof is shown in FIG. 6. FIG. 6(a) shows the cells in a Sub-G$_1$ phase, FIG. 6(b) shows the cells in a G$_0$/G$_1$ phase, FIG. 6(c) shows the cells in an S phase, and FIG. 6(d) shows the cells in a G$_2$/M phase. In each graph, a lateral axis indicates a treatment time (hours) and a vertical axis indicates a measurement ratio (%) with respect to the cell number (the total cell number).

As a result, interestingly, the number of cells in the G$_2$/M phase decreased while the number of cells in the S phase increased with the passage of treatment time. This result showed that the hexane extract fraction treatment inhibited the growth of the Jurkat cells by arresting the cell cycle in the S phase.

Further, the Jurkat cells treated with the hexane extract fraction were microscopically observed by staining with a Hoechst dye and a propidium iodide dye to find that a nucleus and mitochondria were hardly collapsed. Further, degradation of DNA was hardly detected after extraction, suggesting that necrosis or apoptosis did not occur. These results showed that the hexane extract fraction of the watermelon sprout had an effect of inducing the cell cycle arrest in the S phase.

[Effect of Substances Isolated from Watermelon Sprout Ethanol Eluate by Using Various Solvents on Growth of Human T-Cell Leukemia Cell Line Jurkat Cell]

The Hexane Fr. (the hexane extract fraction) was subjected to preparative HPLC to isolate and detect phytol, lutein, 22-dehydrocholesterol, and linolenic acid as main components. These components were examined for the growth inhibitory effect on the Jurkat cells. The Jurkat cells were treated with each component at final concentrations of 10, 25, and 50 µM and the number of cells was counted after 24, 48, and 72 hours.

Figure 7:
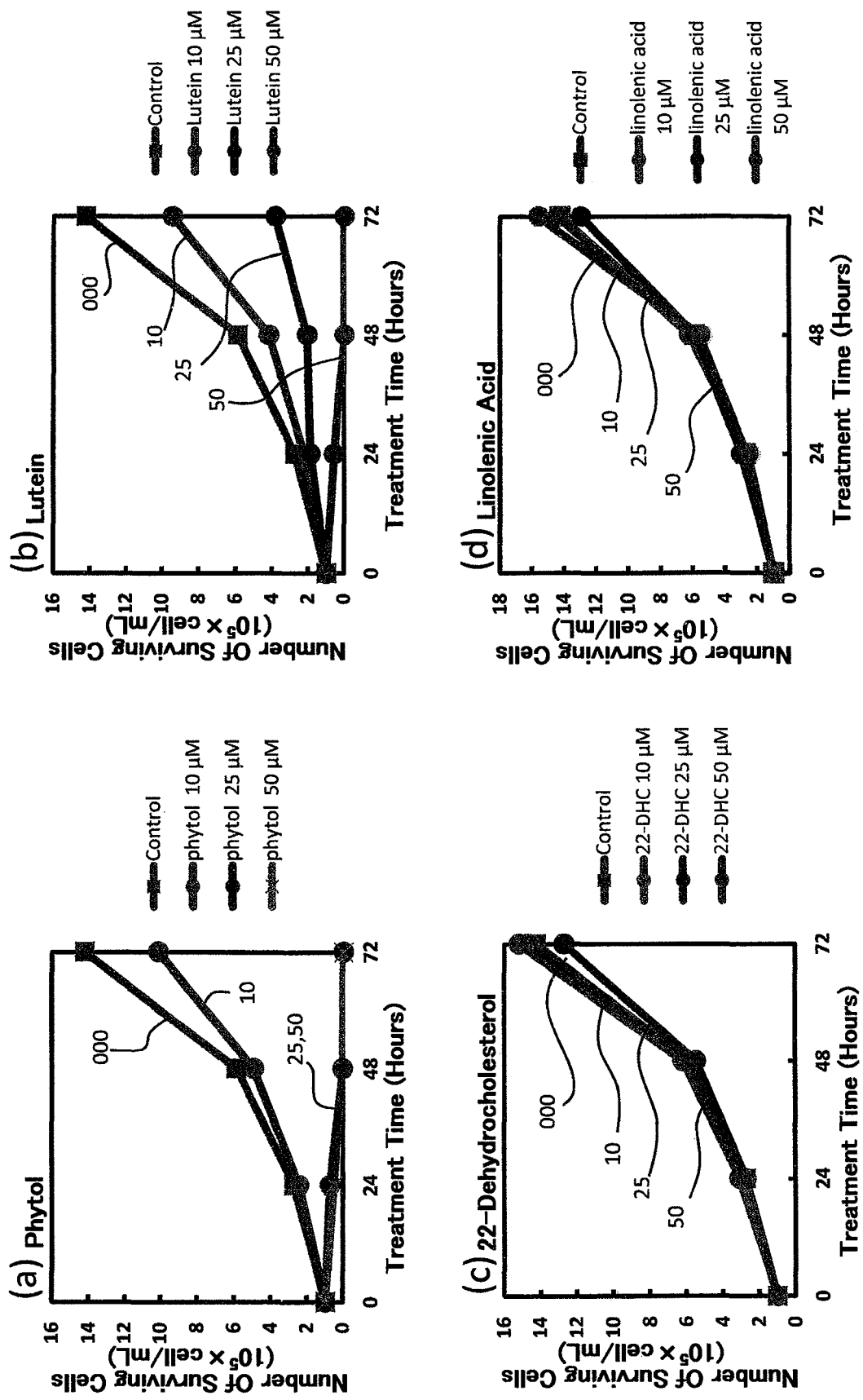
FIG. 7 is graphs showing effects of substances of the ethanol eluate of the watermelon sprout isolated by using various solvents on the growth of the human T-cell leukemia cell line Jurkat cell.

The results thereof are shown in FIG. 7. FIG. 7(a) shows the result of phytol, FIG. 7(b) shows the result of lutein, FIG. 7(c) shows the result of 22-dehydrocholesterol, and FIG. 7(d) shows the result of linolenic acid. In each graph, a lateral axis indicates a treatment time (hours) and a vertical axis indicates the number of surviving cells (10$^5$×cells/mL). Symbols represent as follows: (10): final concentration of 10

μM, (25): final concentration of 25 μM, (50): final concentration of 50 μM, and (000): control.

Referring to FIG. 7, it was confirmed that phytol (FIG. 7(a)) and lutein (FIG. 7(b)) had the significant growth inhibitory activity. On the other hand, 22-dehydrocholesterol (FIG. 7(c)) and linolenic acid (FIG. 7(d)) hardly inhibited the growth of the Jurkat cells. $IC_{50}$ values of phytol and lutein in the inhibition of the growth of the Jurkat cells were calculated to be 12.8 μM and 22.6 μM, respectively.

Figure 8:
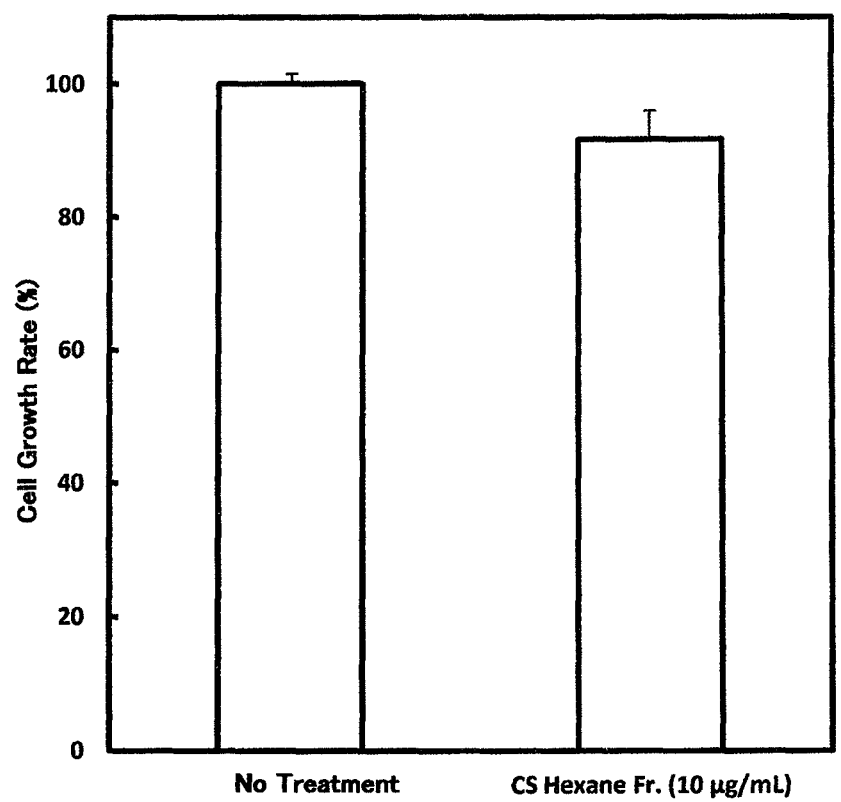
FIG. 8 is a graph showing an effect of the watermelon sprout-hexane eluate treatment on the growth of a normal lymphoid cell.

Next, an effect of the Hexane Fr. (the hexane extract fraction) on a normal lymphoid cell was examined. The lymphoid cells were treated with the Hexane Fr. at a final concentration of 10 μg/mL and its cell growth inhibitory effect was examined at 72 hours after treatment. The result thereof is shown in FIG. 8. A lateral axis indicates the treatment liquid used (CS Hexane Fr. and no treatment) and a vertical axis indicates a cell growth rate (%). The cell growth rate was expressed as a percent relative to an increase in the number of untreated cells. It was observed that cell growth of the hexane eluate treated cells (CS Hexane Fr.) was substantially the same as that of the untreated cells. This result confirmed that the hexane extract fraction did not exhibit the growth inhibitory effect on the normal cell.

[Effect of Watermelon Sprout-Hexane Dissolved Matter Treatment on Growth of Various Cancer Cells]

The growth inhibitory effect on various cancer cells was examined by a WST-1 method to obtain $IC_{50}$ values shown in Table 1. The results suggested that, although sensitivity slightly varied depending on types of cancer cells, the watermelon sprout-hexane dissolved matter treatment was effective on any types of the examined cancer cells.

TABLE 1

| Cell Lines | Growth Inhibitory Activity ($IC_{50}$ Value) |
|---|---|
| Human T-Cell Leukemia Cell Line Jurkat Cell | 4.7 μg/mL |
| Human Cervical Cancer-Derived Cell Line Hela Cell | 6.2 μg/mL |
| Human Alveolar Basal Epithelial Adenocarcinoma A549 | 38.2 μg/mL |
| Human Gastric Cancer-Derived Cell Line KATOIII Cell | 23.4 μg/mL |
| Human Hepatoma-Derived Cell Line HepG2 Cell | 26.7 μg/mL |

Next, the growth inhibition of the Jurkat cells caused by phytol and lutein was further investigated. As shown in FIG. 6 and FIG. 7, the growth inhibition of the Jurkat cells was caused by the induction of the cell cycle arrest in the S phase during cell division. Thus, it was further investigated how phytol induced the cell cycle arrest in the S phase. Specifically, protein expression of a molecule that controls the S phase of the cell cycle was examined by a Western blot method.

As a result, it was found that an expression level of Cyclin A involved in DNA replication was reduced. Reduction of the expression level of Cyclin A stops a transition from the S phase to the $G_2$ phase. Thus, it was considered that the phytol treatment reduced the expression level of Cyclin A to induce S phase arrest.

Figure 9:
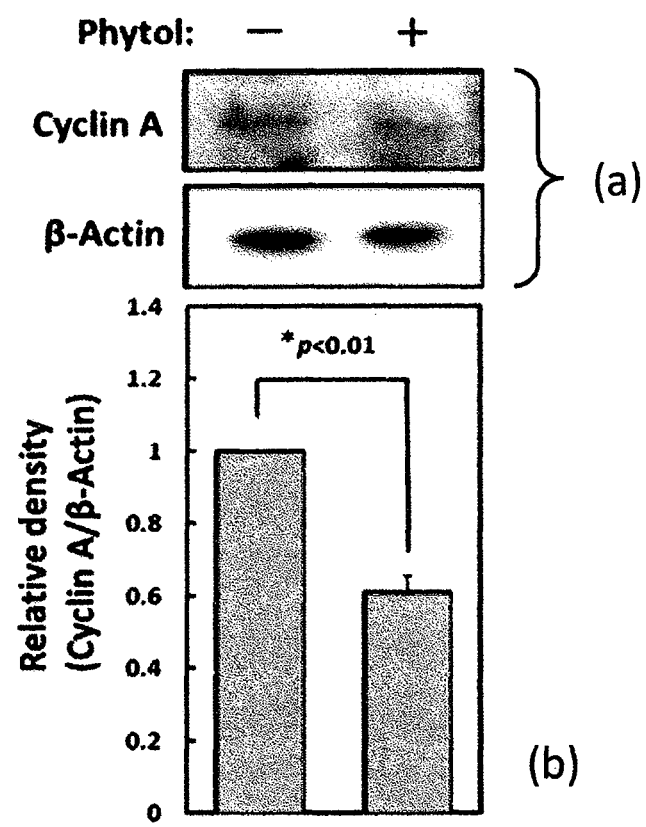
FIG. 9 is a diagram showing a result of a Western blotting method detecting a protein Cyclin A that is extracted from the Jurkat cells in S phase after treated with phytol.

FIG. 9(a) shows a result of the Western blotting method detecting a protein Cyclin A that is extracted from the Jurkat cells in the S phase after treated with phytol. Results of Cyclin A and β-Actin are shown with a phytol treatment (Phytol(+)) and without a phytol treatment (Phytol(−)).

Further, in FIG. 9(b), the result of the Western blot shown in FIG. 9(a) was subjected to background correction using an image analysis software imageJ and then subjected to a densitometry analysis to obtain a ratio of a band density of Cyclin A relative to that of β-Actin. In evaluating data, a value of Phytol(+) was calculated by taking a value of Phytol(−) as 1 and represented as a mean±standard deviation (n=5). Comparison between Phytol(−) and Phytol(+) was tested by a Tukey-Kramer method (p<0.01).

Referring to FIG. 9(a), β-Actin was measured as an endogenous control. β-Actin was detected with an equal concentration regardless of the phytol treatment. On the other hand, Cyclin A was detected with a higher intensity without the phytol treatment (Phytol(−)) than that with the phytol treatment (Phytol(+)). This showed that the expression of Cyclin A was suppressed by the phytol treatment.

From the above-described data, it was found that phytol suppressed the expression of Cyclin A in the Jurkat cancer cells to induce the cell cycle arrest in the S phase. On the other hand, phytol does not exhibit the growth inhibitory effect on the normal cell as shown in FIG. 8. Thus, it was found that phytol had a function of selectively inhibiting only the cancer cell.

As described above, the hexane extract fraction of the watermelon sprout had the effect of inhibiting the growth of the various cancer cells. Further, it was found that the main components causing such an effect were phytol and lutein. Further, these components (including the hexane extract fraction of the watermelon sprout) do not exhibit the effect of inhibiting the cell growth of the normal cell. That is, the effective component of the present invention has the effect of specifically inhibiting the growth of the cancer cell. This means that the present invention can provide the anticancer pharmaceutical composition with fewer side effects.

INDUSTRIAL APPLICABILITY

The effective component of the present invention can be suitably used as a processed food and pharmaceutical composition having a prophylactic or therapeutic effect on cancer.

The invention claimed is:

1. A cancer cell growth inhibitor comprising an effective amount of a hexane extract fraction of a watermelon sprout.

2. The cancer cell growth inhibitor according to claim 1, further comprising a diluent, a lubricant, a binder, a dispersant, a saturant, a colorant, a sweetener, a wetting agent, and a combination thereof.

3. The cancer cell growth inhibitor according to claim 1, further comprising a carrier.

4. A method for producing a cancer cell growth inhibitor, comprising:
   washing and crushing a watermelon sprout as a pretreatment;
   obtaining an extract liquid by immersing the crushed watermelon sprout in a nonpolar extraction solvent; and
   filtering the extract liquid to produce the cancer cell growth inhibitor of claim 1.

5. The method for producing a cancer cell growth inhibitor according to claim 4, wherein
   obtaining the extract liquid includes:
   eluting the crushed watermelon sprout with ethanol to obtain an ethanol eluate;
   redissolving the ethanol eluate with distilled water to obtain a distilled water dissolved matter; and
   dissolving the distilled water dissolved matter with hexane.

6. A processed food comprising an effective amount of a hexane extract fraction of a watermelon sprout.

7. A method for producing a processed food, comprising:
washing and crushing a watermelon sprout as a pretreatment;
obtaining an extract liquid by immersing the crushed watermelon sprout in a nonpolar extraction solvent; and
filtering the extract liquid to produce the processed food of claim 6.

8. The method for producing a processed food according to claim 7, wherein
obtaining the extract liquid includes:
eluting the crushed watermelon sprout with ethanol to obtain an ethanol eluate;
redissolving the ethanol eluate with distilled water to obtain a distilled water dissolved matter; and
dissolving the distilled water dissolved matter with hexane.

\* \* \* \* \*